US00PP15030P2

(12) United States Plant Patent
Yomo et al.

(10) Patent No.: US PP15,030 P2
(45) Date of Patent: Jul. 20, 2004

(54) SALVIA PLANT NAMED 'SUNSARUKI'

(50) Latin Name: *Salvia jamensis*
Varietal Denomination: Sunsaruki

(75) Inventors: Yasunori Yomo, Kawasaki (JP); Takuro Ishihara, Youkaichi (JP)

(73) Assignee: Suntory Flowers, Lmtd., Tokyo (JP)

( * ) Notice: Subject to any disclaimer, the term of this patent is extended or adjusted under 35 U.S.C. 154(b) by 0 days.

(21) Appl. No.: 10/716,055

(22) Filed: Nov. 18, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of Salvia plant named 'Sunsaruki', characterized by its upright and relatively compact plant habit; freely basal branching habit; dense and bushy plant form; freely flowering habit; pale yellow-colored flowers; and tolerance to high and low temperatures.

1 Drawing Sheet

Botanical classification/cultivar designation: *Salvia jamensis* cultivar Sunsaruki.

BACKGROUND OF THE INVENTION

The present Invention relates to a new and distinct cultivar of Salvia plant, botanically known as *Salvia jamensis,* and hereinafter referred to by the name 'Sunsaruki'.

The new Salvia is a product of a planned breeding program conducted by the Inventors in Yokaichi-shi, Shiga, Japan. The objective of the breeding program was to create new compact Salvia cultivars with bushy growth habit and numerous flowers with attractive coloration.

The new Salvia originated from a cross-pollination made by the Inventors in April, 1998 of a proprietary Salvia selection identified as code number 97S34-2, not patented, as the female, or seed, parent with the *Salvia jamensis* cultivar La Luna, not patented, as the male, or pollen, parent. The new Salvia was discovered and selected by the Inventors as a single flowering plant within the progeny of the stated cross-pollination grown in a controlled environment in Yokaichi-shi, Shiga, Japan.

Asexual reproduction of the new cultivar by cuttings and divisions taken at Yokaichi-shi, Shiga, Japan, since September, 2000, has shown that the unique features of this new Salvia are stable and reproduced true to type in successive generations.

SUMMARY OF THE INVENTION

Plants of the cultivar Sunsaruki have not been observed under all possible environmental conditions. The phenotype may vary somewhat with variations in environment such as temperature and light intensity without, however, any variance in genotype.

The following traits have been repeatedly observed and are determined to be the unique characteristics of 'Sunsaruki'. These characteristics in combination distinguish 'Sunsaruki' as a new and distinct Salvia cultivar:

1. Upright and relatively compact plant habit.
2. Freely basal branching, dense and bushy plant form.
3. Freely flowering habit.
4. Pale yellow-colored flowers.
5. Tolerant to high and low temperatures.

Plants of the new Salvia differ from plants of the parents primarily in flower color as plants of the female parent selection have red purple-colored flowers and plants of the male parent, the cultivar La Luna, have yellow green-colored flowers.

Plants of the new Salvia differ from plants of the Salvia cultivars Sunsarupin, U.S. Plant patent application Ser. No. 10/716,049, and Sunsaruoro, U.S. Plant patent application Ser. No. 10/716,056 primarily in flower color.

Plants of the new Salvia can be compared to plants of the Salvia cultivar Orchestra Red, not patented. In side-by-side comparisons conducted in Yokaichi-shi, Shiga, Japan, plants of the new Salvia differed from plants of the cultivar Orchestra Red in the following characteristics:

1. Plants of the new Salvia were more compact than plants of the cultivar Orchestra Red.
2. Plants of the new Salvia had shorter internodes and were bushier than plants of the cultivar Orchestra Red.
3. Plants of the new Salvia had shorter leaves than plants of the cultivar Orchestra Red.
4. Plants of the new Salvia had larger flowers than plants of the cultivar Orchestra Red.
5. Plants of the new Salvia had more flowers per lateral stem than plants of the cultivar Orchestra Red.
6. Plants of the new Salvia and the cultivar Orchestra Red differed in flower color as plants of the cultivar Orchestra Red had red-colored flowers.
7. Plants of the new Salvia were tolerant to lower temperatures than plants of the cultivar Orchesta Red.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Salvia.

The photograph at the top of the sheet comprises a side perspective view of a typical flowering plant of 'Sunsaruki' grown in a container.

The photograph at the bottom of the sheet comprises a close-up view of typical flowers of 'Sunsaruki'.

DETAILED BOTANICAL DESCRIPTION

Plants shown in the aforementioned photographs and used in the following description were grown under conditions which closely approximate commercial production conditions from April to October, 2002 in a polyethylene-covered greenhouse in Yokaichi-shi, Shiga, Japan. During the production of the plants, day temperatures were about 25° C. and night temperatures were about 20° C. Plants in the photographs and used for the description were about six months old when the photographs and description were taken.

In the following description, color references are made to The Royal Horticultural Society Colour Chart, 2001 Edition, except where general terms of ordinary dictionary significance are used.

Botanical classification: *Salvia jamensis* cultivar Sunsaruki.

Parentage:

*Female, or seed, parent.*—Proprietary selection of *Salvia jamensis* identified as code number 97S34-2, not patented.

*Male, or pollen, parent.*—*Salvia jamensis* cultivar La Luna, not patented.

Propagation:

*Type.*—By cuttings.

*Time to initiate roots.*—Summer: About 7 days at 25° C. Winter: About 10 days at 20° C.

*Time to produce a rooted young plant.*—Summer: About 30 days at 20 to 30° C. Winter: About 40 days at 15 to 20° C.

*Root description.*—Fine, fibrous, freely branching and light brown in color.

Plant description:

*Form.*—Perennial. Mostly upright and relatively compact plant habit; narrow inverted triangle. Freely basal branching with about 20 flowering stems per plant; dense and bushy plant habit; vigorous growth habit. Flowers arranged in verticillasters on spikes.

*Plant height.*—About 55 cm.

*Plant width.*—About 57 cm.

*Flowering stem description* (*peduncles*).—Length: About 47 cm. Diameter: About 3 mm. Internode length: About 4.5 cm. Strength: Strong. Texture: Smooth, glabrous. Color: 144A.

*Foliage description.*—Arrangement: Opposite, simple. Length: About 2.9 cm. Width: About 1.6 mm. Shape: Ovate. Apex: Acute. Base: Obtuse. Margin: Serrate to crenate. Texture, upper and lower surfaces: Rough; waxy; glabrous. Venation pattern: Pinnate. Color: Developing and fully expanded foliage, upper surface: 138A. Developing and fully expanded foliage, lower surface: 138B. Petiole: Length: About 1.3 cm. Diameter: About 0.7 mm. Texture, upper and lower surfaces: Smooth, glabrous. Color: 138A.

Flower description:

*Flower arrangement and shape.*—Single bilabiate flowers in verticillasters on spikes; flowers face upright and outwardly. Freely flowering, about 12 flowers and flower buds per spike.

*Natural flowering season.*—Continuous from spring to late autumn in Japan.

*Flower longevity on the plant.*—Individual flowers last about two to five days on the plant. Flowers not persistent.

*Fragrance.*—Faintly fragrant; sweet.

*Flower buds.*—Length: About 1.5 mm. Diameter: About 3 mm. Shape: Oblong. Color: 12A.

*Inflorescence size.*—Length: About 20 cm. Diameter: About 4.5 cm.

*Flowers.*—Diameter: About 1.9 cm. Depth (height): About 3.2 cm.

*Petals.*—Arrangement: Bilabiate; one upper lip and one lower lip with two lobes; lips fused at the base. Length: Upper petal: About 9 mm. Lower petal: About 1.1 cm. Width: Upper petal: About 3 mm. Lower petal: About 1.3 cm. Shape: Upper petal: Broadly elliptic; hooded. Lower petal: Roughly orbicular. Apex: Upper petal: Hooked. Lower petal: Two-lobed. Margin, upper and lower petals: Entire. Texture, upper and lower petals: Satiny, smooth. Color, upper and lower petals: When opening and fully opened, upper surface: 8D. When opening and fully opened, lower surface: 8D.

*Sepals.*—Arrangement: Two sepals fused into a tube. Length: About 3 mm. Width: About 2.7 mm. Shape: Triangular. Apex: Acute. Margin: Entire. Color, upper and lower surfaces: 144B overlain with 143A.

*Pedicels.*—Strength: Moderately strong. Length: About 1.5 mm. Diameter: About 0.3 mm. Aspect: About 40° from vertical. Texture: Smooth, glabrous. Color: 147A.

*Reproductive organs.*—Stamens: Quantity per flower: Two. Anther shape: Ovate. Anther length: About 8 mm. Anther color: 15C. Pollen amount: Moderate. Pollen color: 15A. Pistils: Quantity per flower: One. Pistil length: About 2.7 cm. Stigma shape: Two-parted. Stigma color: 48D. Style length: About 2.5 cm. Style color: 155C. Ovary color: 3C.

*Seed/fruit.*—Seed and fruit production has not been observed.

Disease/pest resistance: Plants of the new Salvia have not been noted to be resistant to pathogens and pests common to Salvia.

Temperature tolerance: Plants of the new Salvia have been observed to tolerate temperatures from −10 to 40° C.

It is claimed:

1. A new and distinct cultivar of Salvia plant named 'Sunsaruki', as illustrated and described.

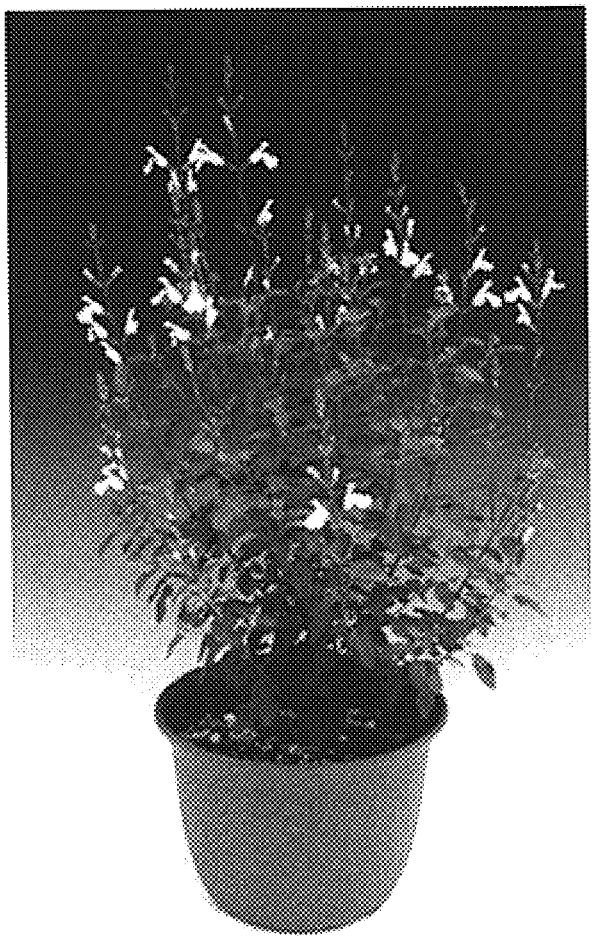
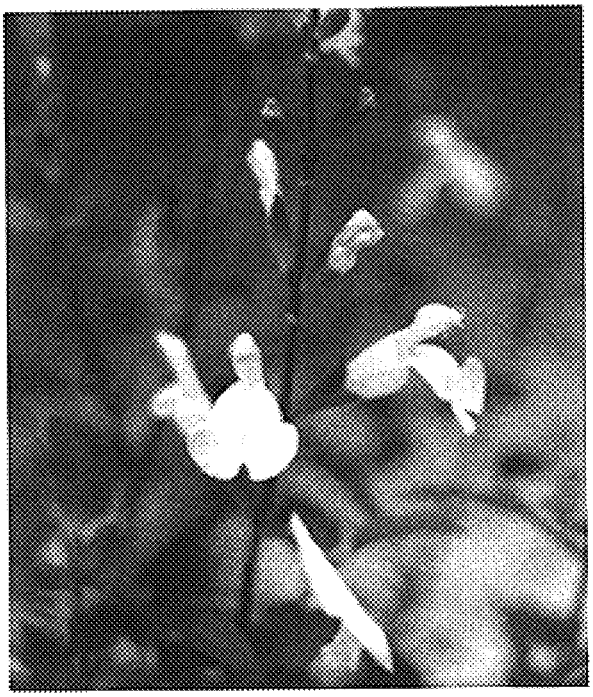

* * * * *